United States Patent [19]
Gorfinkel et al.

[11] Patent Number: 5,784,157
[45] Date of Patent: Jul. 21, 1998

[54] METHOD AND APPARATUS FOR IDENTIFYING FLUOROPHORES

[75] Inventors: Vera Gorfinkel, Kassel, Germany; Serge Luryi, Stony Brook, N.Y.

[73] Assignee: The Research Foundation of State University of New York, Albany, N.Y.

[21] Appl. No.: 561,368

[22] Filed: Nov. 21, 1995

[51] Int. Cl.$^6$ .................................................. G01J 3/30
[52] U.S. Cl. ...................... 356/318; 356/417; 250/458.1; 250/459.1
[58] Field of Search .................... 356/318, 417, 356/335–343, 244; 250/458.1, 459.1, 461.1, 461.2; 128/633, 634

[56] References Cited

U.S. PATENT DOCUMENTS

| | | | |
|---|---|---|---|
| 4,800,885 | 1/1989 | Johnson | 128/633 |
| 4,937,457 | 6/1990 | Mitchell | 250/458.1 |
| 5,032,714 | 7/1991 | Takahashi et al. | 250/458.1 X |
| 5,128,019 | 7/1992 | Karpf et al. | |
| 5,244,810 | 9/1993 | Gottlieb | 128/634 X |
| 5,274,225 | 12/1993 | Gorfinkel et al. | |
| 5,281,825 | 1/1994 | Berndt et al. | 250/458.1 |
| 5,300,789 | 4/1994 | Gorfinkel et al. | |
| 5,311,526 | 5/1994 | Gorfinkel et al. | |
| 5,321,253 | 6/1994 | Gorfinkel et al. | |
| 5,365,326 | 11/1994 | Chrisman et al. | 356/342 |
| 5,422,904 | 6/1995 | Gorfinkel et al. | |

FOREIGN PATENT DOCUMENTS

| | | |
|---|---|---|
| 263037 | 4/1988 | European Pat. Off. |
| 371953 | 6/1990 | European Pat. Off. |
| 476792 | 3/1992 | European Pat. Off. |
| 563998 | 10/1993 | European Pat. Off. |
| WO9418547 | 8/1994 | WIPO |

OTHER PUBLICATIONS

Tran et al "Acousto-optic Tunable . . . Spectroscopy" Analytical Chemistry, Nov. 15, 1992, pp. 2775–2782 No. 22, vol. 64.

Ferdinand, P. et al., "Optical Fibre Bragg Grating Sensors for Structure Monitoring within the Nuclear Power Plants", SPIE vol. 2424, pp. 11–20.

Town, G.E. et al., "Wide–Band Fabry–Perot–Like Filters in Optical Fiber", IEEE Photonics Technology Letters, 7 (1995) No. 1, pp. 78–80.

"Compact Backscatter Fiber Optic Systems For Submicroscopic Particle Sizing," by H.S. Dhadwal et al., *Particulate Science and Technology: An International Journal*, vol. 12, pp. 139–148 (1994).

"Modeling of Dispersive Microwave FET Devices Using a Quasi-Static Approach," by G. Kompa, *International Journal of Microwave and Millimeter–Wave Computer–Aided Engineering*, vol. 5, No. 3, pp. 173–194 (1995).

"Fluorometric Photodiode Array Detection in Capillary Electrophoresis," by D.F. Swaile et al., *J. Microcolumn Separations*, vol. 1, No. 3, pp. 155–158 (1989).

"Coherent Fiber Optic Sensors for Early Detection of Cataractogenesis in a Human Eye Lens," by H.S. Dhadwal et al., *Optical Engineering*, vol. 32, No. 2, pp. 233–238 (Feb. 1993).

(List continued on next page.)

*Primary Examiner*—K. Hantis
*Attorney, Agent, or Firm*—Baker & Botts, L.L.P.

[57] ABSTRACT

The present invention is a unique method for identifying the presence, and preferably the identity, of a fluorophore by optically stimulating one or more fluorophores with an optical signal which has been modulated in intensity in the time domain. The stimulated fluorophore produces a resulting fluorescence which is demodulated to produce an electrical signal corresponding to the intensity modulation of the fluorescence. Finally, the electrical signal is compared to the modulation of the optical signal to determine whether or not the fluorophore is present. The present method can be used alone or in conjunction with known methods of optically analyzing fluorescence of fluorophores to determine the presence of fluorophores.

24 Claims, 5 Drawing Sheets

OTHER PUBLICATIONS

"High–Frequency Modualtion of a QW Diode Laser by Dual Modal Gain and Pumping Current Control," by Gorfinkel et al., *Proceedings of International Electron Devices Meeting,* (IEDM 1993 Washington, D.C.), pp. 933–936 (1993).

"Rapid Modualtion of Interband Optical Properties of Quantum Wells by Intersubband Absorption," by Gorfinkel et al., *Appl. Phys. Lett.,* vol. 60, pp. 3141–3143 (Jun. 1992).

"High–Frequency Modulation and Suppression of Chirp in Semiconductor Lasers," by Gorfinkel et al., *Appl. Phys. Lett.,* vol. 62, pp. 2923–2925 (Jun. 1993).

"Fast Data Coding Using Modulation of Interband Optical Properties by Intersubband Absorption In Quantum Wells," by Gorfinkel et al., *Quantum Well Intersubband Transition Physics and Devices,* pp. 533–545 (1994).

"Four–Component Determinants Using Phase–Resolved Fluorescence Spectroscopy," by F.V. Bright et al., *Anal. Chem.,* vol. 57, pp. 55–58 (1985).

"Miniature Fluorometric Photodiode Array Detection System for Capillary Chromatography," by J.C. Gluckman et al., *Anal. Chem.,* vol. 57, pp. 1546–1552 (1985).

"Charge–Coupled Device Fluorescence Detection for Capillary–Zone Electrophoresis (CCD–CZE)," by Y.F. Cheng et al., *Applied Spectroscopy,* vol. 44, No. 5, pp. 755–765 (1990).

"Lifetime–Selective Fluorescence Imaging Using an RF Phase–Sensitive Camera," by J.R. Lakowicz et al., *Rev. Sci. Instrum.,* vol. 62, pp. 1727–1734 (Jul. 1991).

"DNA Sequence Analysis of Five Genes; tnsA, B, C, D and E, Required for Tn7 Transportation," by C. Flores et al., *Nucleic Acids Res.,* vol. 18, No. 4, pp. 901–911 (1990).

"Fluorescence Detection in Capillary Zone Electrophoresis Using a Charge–Coupled Device with Time–Delayed Integration," by J.V. Sweedler et al., *Anal. Chem.,* vol. 63, pp. 496–502 (1991).

"Photon Burst Detection of Single Near–Infrared Fluorescent Molecules", by S.A. Soper et al., *Anal. Chem.,* vol. 65, pp. 740–747 (1993).

"Steady–State and Picosecond Laser Fluorescence Studies of Nonradiative Pathways in Tricarbocyanine Dyes: Implications to the Design of Near–IR Fluorochromes with High Fluorescence Efficiencies," by S.A. Soper et al., *J. Am. Chem. Soc.,* vol. 116, pp. 3744–3752 (1994).

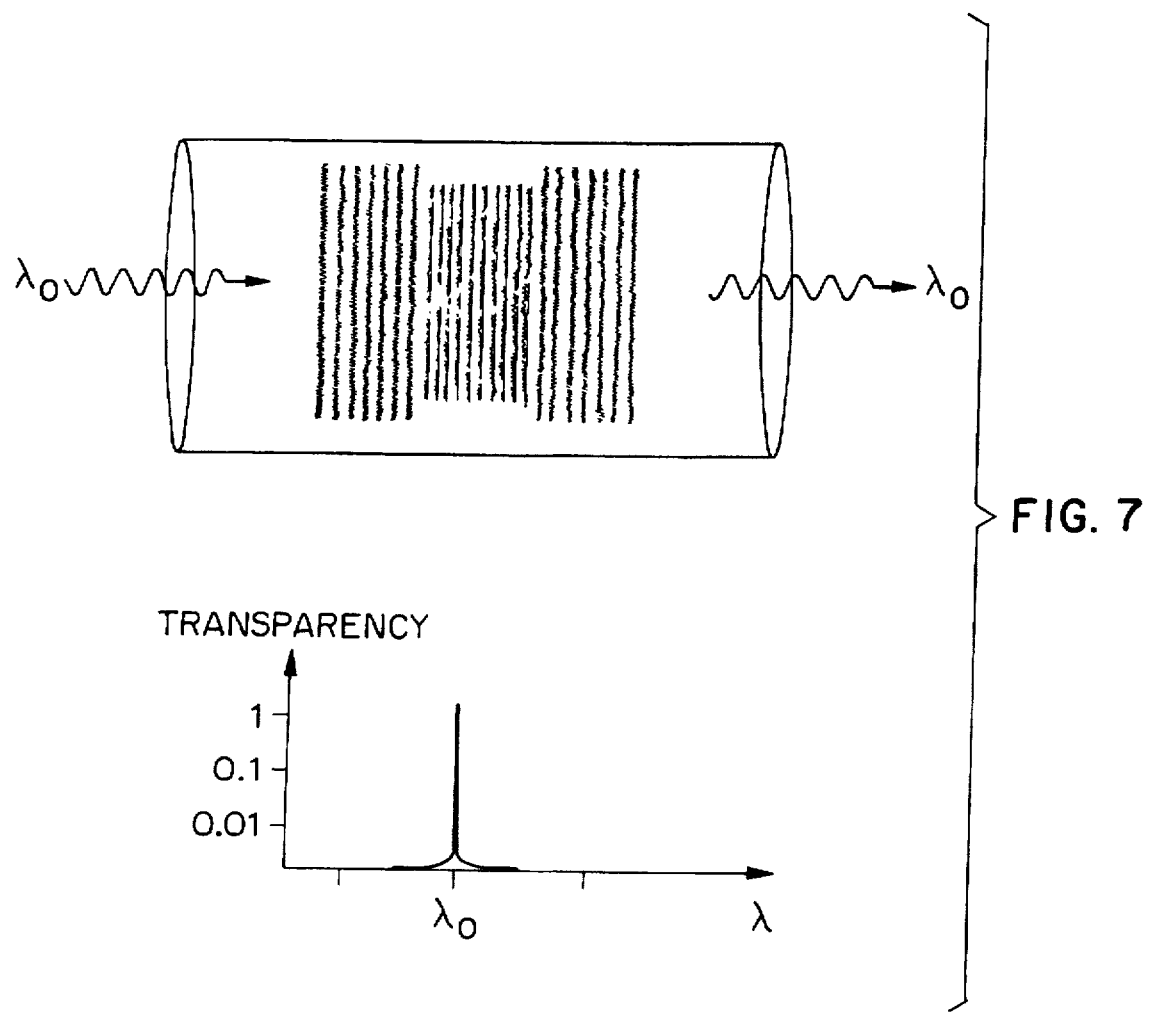

METHOD AND APPARATUS FOR IDENTIFYING FLUOROPHORES

The present invention relates to the art of information retrieval using substances which respond to radiation, and, in particular, to identification of the presence of a fluorophore in a medium.

BACKGROUND OF THE INVENTION

Certain substances are known to possess a unique quality of producing light in response to being irradiating. These substances, which are referred to herein collectively as fluorophores, produce light after being excited by radiant energy. This property is referred to as fluorescence.

Fluorescence occurs when electrons, which have been displaced to excited states by energy absorbed during radiation, return to lower energy levels. Energy in the form of electromagnetic quanta is given off when the electrons return to lower energy levels. Fluorescence begins when the fluorophore is irradiated and ends when irradiation ceases, with a short time delay, typically 0.1-10 ns. The intensity of fluorescence is usually proportional to intensity of irradiation, unless the irradiation intensity is too high.

The ability of certain substances to fluoresce has been found useful in conducting chemical and biological analysis. In U.S. Pat. No. 5,171,534 to Smith, et al., a system for electrophoretic analysis of DNA fragments produced in DNA sequencing is disclosed, wherein characterization of the fragments depends on the fluorescent property of four chromophores tagged to the DNA fragments. The Smith, et al. technique relies on the optical characteristics of the emission spectra of the four fluorophores used as tags. Consequently, the Smith, et al. technique suffers from many shortcomings associated with analysis which depends on the optical properties of emission spectra.

For example, the Smith, et al. technique requires dyes which must have high extinction coefficients and/or reasonably high quantum yields for fluorescence. Apparatus required to identify the fluorophore-tagged fragments is complex and requires accurate optical means to distinguish the different emission spectra. Moreover, Smith, et al. is inherently inefficient since it requires reduction of portions of the optical signal by refining the observed emission using filtration and reducing scattered light emission(s).

It is, therefore, an object of the present invention to eliminate the drawbacks of using the optical characteristics of fluorescence as a means for conducting chemical and biological analysis.

It is another object of the present invention to conduct high speed automated data acquisition using the fluorescence characteristics of fluorophores with a high degree of confidence and without the need for human intervention.

These and other objects will be apparent to those skilled in the art in view of the following disclosure. Accordingly, the scope of the claimed invention is not to be limited by the recitation set forth hereinabove.

SUMMARY OF THE INVENTION

The present invention is a new method of identifying the presence of a fluorophore. The new method utilizes the unique characteristic of fluorophores to emit light in response to incident radiation. According to the present invention an optical signal having a time-domain-modulated intensity is used to irradiate a substance which contains a fluorophore. The fluorophore must be in an environment in which it can be freely excited and fluoresce, and the resulting fluorescence must be detectable by an optically sensitive receiver.

The optical signal must also be capable of exciting the fluorophore, and is preferably a monochromatic light having a known wavelength. The fluorophore produces a responsive fluorescence which has an intensity also modulated in the time-domain corresponding to the modulation of the optical signal which is used to excite the fluorophore.

The time-modulated fluorescence is then demodulated by a optically sensitive receiver, such as a photodetector to produce a response signal, e.g., an electrical signal or an accoustical signal, which, as a function of time, corresponds to the intensity of the fluorescence in the time-domain.

In the broadest sense, the invention contemplates using the information to determine one or more characteristics of the fluorophore and/or its environment. Otherwise, the resulting electrical signal can be compared to the time-domain-modulation used to modulate the optical signal whereby the presence of the fluorophore can be determined. In a preferred embodiment of the identity of fluorophore can also be determined.

The optical signal used to excite the fluorophore can be modulated with an analog characteristic or can be digitally modified.

Information regarding the fluorophore can also be obtained by phase-resolved measurements employing multiple frequencies. Thus, a fluorophore can be stimulated to reduce fluorescence which has "n" distinguishable time-domain-funtions, wherein n is greater than 1, and wherein the functions are linearly independent in time. The response signal can be analyzed to determine the fluorescence lifetime.

The present invention also includes an apparatus for detecting fluorophores which includes a source of optical signal capable of exciting fluorophores, e.g., a laser, a modulator for modulating the optical signal and connected to the source for producing the signal in order to impose the time-domain-modulation on the signal. The apparatus also includes a fluorophore substance holder to secure the fluorophore material and make it available for irradiation and also for detection by a detector. A demodulator is connected to the holder to detect the fluorescence from the excited fluorophores and for conversion to a response signal such as an electrical signal. Preferably the demodulator is a photoreceiver.

In one preferred embodiment of the invention, a comparator is also used in the apparatus and is connected to the demodulator for receipt of the signal, and can also be connected to the modulator for comparing the modulation signal to the electrical signal in order to determine the presence of the fluorophore.

In one preferred embodiment of the present invention, the apparatus can include an integrated optical probe which has at least one transmitter optical fiber and at least one receiver optical fiber and is fixed in relationship to the fluorophore substance holder in order to introduce incident radiation on the substance and to detect fluorescence resulting from excitation of the fluorophores.

Furthermore, the apparatus can include an optical filter element interposed between the fluorophore holder and the demodulator. This can be part of the optical probe or can be separate. The optical filter element can be an optical fiber provided with a refractive index grading profile, to produce, e.g., either a Bragg reflector, or a Fabry-Perot étalon.

As a result of the present invention, the ability to determine the presence of a fluorophore is significantly increased.

The present technique enhances the signal-to-noise ratio by more than tenfold, and increases the confidence level of base pair identification in automated DNA sequencing.

Furthermore, a high-throughput miniaturized automated data acquisition system can be provided which has a modular structure designed for use with most fluorescence-based electrophotetic arrangements.

Consequently, high confidence level, low cost DNA sequencing systems are achievable as a result of the present invention.

These and other advantages will be appreciated by those skilled in the art in view of the detailed description and the drawings set forth herein. The scope of the invention will be pointed out in the claims appended hereto.

BRIEF DESCRIPTION OF THE DRAWINGS

FIG. 7 depicts a fiber-receiver with a refractive index grading forming a Fabry-Perot resonator tuned to a desired wavelength of fluorescent response.

DETAILED DESCRIPTION OF THE INVENTION

Figure 1:
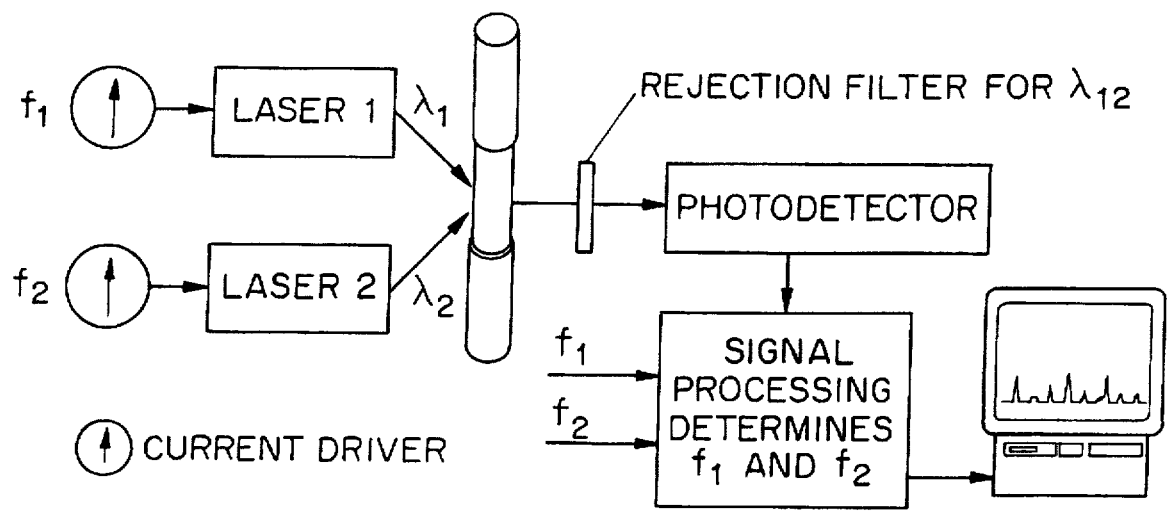
FIG. 1 is a schematic of the data acquisition system in accordance with the present invention which utilizes multi-color excitation by intensity-modulated lasers.

The present invention is a unique method of identifying the presence of a fluorophore which is particularly useful in conducting analysis especially in the area of biotechnology. A fluorophore as used herein means any moiety capable of emitting fluorescence in response to an optical signal. The present invention also requires that the fluorophore be in an environment in which it can be freely excited to produce its characteristic fluorescence.

The present invention is of particular interest in the area of automated DNA sequencing. The development of reliable methods for sequence analysis of DNA and RNA is key to the success of recombinant DNA and genetic engineering technology. Previous DNA sequencing methods known to date have relied on, among other things, the optical characteristics of fluorophores which are used to tag DNA fragments. As previously mentioned, U.S. Pat. No. 5,171,534 to Smith, et al. discloses irradiating DNA fragments tagged with fluorophores to produce a characteristic fluorescence. The optical characteristics of the fluorescence are then analyzed to determine the presence of the fluorophore, and, consequently, information relating to the DNA fragment being analyzed.

Many drawbacks exist with respect to the known technology, especially since the technique involves relatively inefficient use of the fluorescence capability of the fluorophore as well as reliance on human intervention to interpret data.

In the present invention, however, detailed analysis of DNA sequencing can be conducted completely (to include final base-pair identification) without requirement for human intervention and with a high degree of quantitative confidence.

In accordance with the present invention an optical signal having a modulated intensity in the time domain is used to irradiate a fluorophore which can be excited by the selected signal. Specifically, one or more lasers radiating at a peak wave length of the absorption spectrum of individual labels and modulated as a distinguishable function of time, e.g., sinusoidally at a distinct radio frequency, is used to excite the fluorophores. Separation of the responses from one or more labels is accomplished in the electric domain. The method used herein is non-selective with respect to the wavelength of fluorescence. Consequently, the present technique makes full use of each fluorescent molecule by detecting the entire fluorescent power spectrum emitted by each fluorophore. This is a departure from techniques used in the past, especially the Smith, et al. technique, which rely on detection of a narrow wave length band.

The fluorophores useful in the present invention can be selected from dyes which are available based on criteria known to those skilled in the art. Dyes can be selected based on the feasibility of coupling the dyes to each of the four different dideoxynucleotides, a determination of whether or not the modified nucleotides impacts negatively on DNA synthesis, and whether or not any of the di-nucleotide combinations interfere with the DNA secondary structure, and/or can be used to decrease the problems associated with abnormal DNA migration which occurs during electrophoresis.

In the past, a single radioactive or fluorescent label has been used to identify all bands on the gels. This necessitates that the fragment sets produced in the four synthesis reactions be run on separate gel tracts and leads to problems associated with comparing band mobilities in the different tracts. Clearly this system is inefficient and overcoming the problems associated therewith has been the key accomplishment of the invention by Smith et al. which ensured its wide application. The present invention offers an alternative method for realizing multicolor labeling which accomplishes essentially the same goal and, at the same time, offers several technical advantages, such as higher excitation efficiency of individual fluorophores, and better utilization of the fluorescent radiation. Furthermore, the present detection scheme can be advantageously combined with the known Smith et al. method, so as to enhance the signal to noise ratio to the level where a fully automated readout system becomes practical.

In the present invention, each tagged primer can be paired with one of the dideoxynucleotides and used in the primed synthesis reaction. Representative of such amino-reactive dyes include the following: fluorscein, isothiocyanage (FITC, $\lambda_{max}^{Ex}$=495, $\lambda_{max}^{Em}$=520, $\epsilon_{495}$=8×10$^4$), tetramethyl rhodamine isothiocyanate (TMRITC, $\lambda_{max}^{Ex}$=550, $\lambda_{max}^{Em}$= 578, $\epsilon_{550}$=4×10$^4$), and substituted rhodamine isothiocyanate (XRITC, $\lambda$=580, $\lambda_{max}^{Em}$=604, $\epsilon_{580}$=8×10$^4$) where $\lambda$ is the wavelength in nanometers, Ex is excitation, Em is emission, max is maximum, and $\epsilon$ is the molar extinction coefficient. These are the dyes which were used in the Smith, et al. system. However, it is to be clearly understood that the present invention is not limited by any particular set of dyes and those skilled in the art will undertake to select dyes based on criteria set forth above as well as ease of preparation and other operational and critical criteria. Moreover, the fluorophores are to be maintained in an environment useful to those skilled in the art such as slab-gel, capillary, ultra-thin gel and membrane systems.

Figure 2:
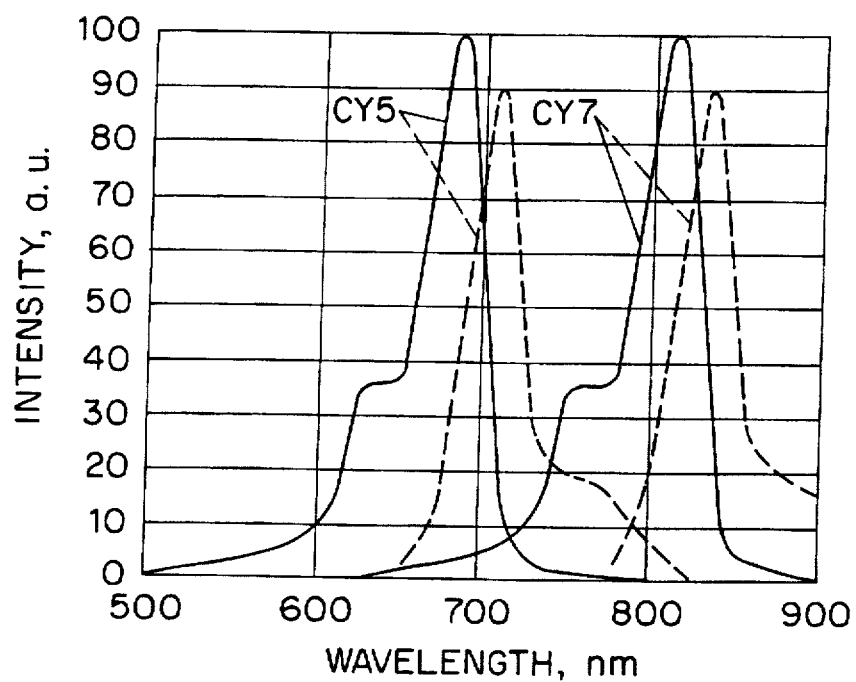
FIG. 2 is a schematic depicting exemplary absorption and fluorescence spectra of two infrared dyes.

In any event, the present invention contemplates the effective coupling of the fluorophore to a nucleotide in a manner which permits the nucleotide to be contained in a medium wherein it can be freely excited and is able to fluoresce uninhibitedly to provide the full spectra of fluorescence. Referring to FIG. 2, the absorption or excitation spectrum and the fluorescence spectrum of two infrared dyes identified as CY5 and CY7 are depicted. The solid lines depict the absorption or excitation spectrum of wavelengths while the dashed lines show the emission or fluorescence spectrum of wavelengths.

FIG. 1 depicts a system in which the technique of the present invention can be implemented. For purpose of explanation, consider that two lasers, laser 1 and laser 2 are modulated in the time domain at frequencies $f_1$ and $f_2$, respectively. Conventional techniques for modulation of semiconductor lasers by varying the pump current are capable of producing modulation frequencies up to approximately 20 GHz. Still higher modulation frequencies can be realized by exploratory techniques, currently under intense development, see, for example, V. B. Gorfinkel, S. Luryi, "High-Frequency Modulation and Suppression of Chirp in Semiconductor Lasers", *Appl. Phys. Lett.*, 62, pp. 2923–2925, (1993); V. B. Gorfinkel, S. Luryi, "Article that comprises a semiconductor laser, and method of operating the article" (dual modulation), U.S. Pat. No. 5,311,526 (1994); V. B. Gorfinkel, S. Luryi, "Article Comprising Means for Modulating the Optical Transparency of a Semiconductor Body, and Method of Operating the Article", U.S. Pat. No. 5,300,789 (1994); V. B. Gorfinkel and S. Luryi, "Fast data coding using modulation of interband optical properties by intersubband absorption in quantum wells", *Quantum Well Intersubband Transition Physics and Devices*, ed. by H. C. Liu, B. (1995); and V. B. Gorfinkel, S. A. Gurevich, "Method of and means for controlling the electromagnetic output power of electrooptic semiconductor devices", U.S. Pat. No. 5,274,225 (1994). Also, techniques for generation of powerful picosecond optical pulses can be found in V. B. Gorfinkel and Serge Luryi, "Rapid modulation of interband optical properties of quantum wells by intersubband absorption", *Appl. Phys. Lett.* 60, pp. 3141–3143 (1992), V. B. Gorfinkel, S. Luryi, "Article that comprises a semiconductor laser, and method of operating the article" (dual modulation), U.S. Pat. No. 5,311,526 (1994), V. B. Gorfinkel, S. Luryi, "Article Comprising Means for Modulating the Optical Transparency of a Semiconductor Body, and Method of Operating the Article", U.S. Pat. No. 5,300,789 (1994), and V. Gorfinkel, G. Kompa, M. Novotny, S. Gurevich, G. Shtengel, I. Chebunina, "High-frequency modulation of a QW diode laser by dual modal gain and pumping current control." *Proceedings of Int. Electronic Dev. Meeting/IEDM'93/*, 5–8 Dec., Washington, D.C., pp. 933–937; (1993). Laser 1 emits a modulated signal having a characteristic wavelength of $\lambda_1$ and laser 2 emits a time-modulated signal having a characteristic wavelength of $\lambda_2$. Infrared dyes CY5 and CY7 are suspended in a medium which permits free excitation and luminescence. A photodetector is situated to receive the full spectrum of fluorescence of each of the fluorophores except the wavelengths lambda 1 and lambda 2 corresponding to the radiation of lasers 1 and 2, respectively. This is accomplished by a rejection filter for the purpose of isolating the photodetector from the scattered and reflected laser radiation. The full spectra of fluorescence is depicted by the dashed lines in FIG. 2.

The photodetector demodulates the full fluorescence spectra and converts the optimal signal to a corresponding electrical signal. The electrical signal can then be processed by the known methods to identify the presence, isolate, or detect the signals at frequencies f1 and f2. The processing can be done in the electrical domain by analog techniques or digitally.

For ideal detection it would be preferable that the excitation spectra of the two dyes were non-overlapping, so that, e.g., the radiation of laser 1 at lambda 1 would excite only fluorophore A and not fluorophore B, while the radiation of laser 2 at lambda 2 would excite only fluorophore B and not fluorophore A. This ideal case would completely eliminate the "cross-talk" or parasitic excitation of a "wrong" fluorophore. The photodetector receives the entire fluorescent radiation from both dyes A and B. The non-fluorescent radiation from lasers 1 and 2 modulated at frequencies f1 and f2, respectively, has been filtered out by the rejection filter. Therefore, the presence in the detected signal of frequency components f1 or f2 would be direct evidence of the presence of fluorophore A or B, respectively.

However, the ideal case may be difficult to realize, because of the absence of suitable fluorophores. Consider, therefore, the more realistic case, when each of the lasers excites both dyes, but to a different degree.

In this case, the concentration of dyes A and B in the observation slot varies in time as $n_A(t)$ and $n_B(t)$. The slot is illuminated by the output $L_1(t)=L_{f1}\exp(2\pi i f_1 t)$ and $L_2(t)=L_{f2}\exp(2\pi i f_1 t)$, of two lasers that have wavelengths $\lambda_1$ and $\lambda_2$, respectively, and are modulated at (radio) frequencies $f_1$ and $f_2$.

This gives rise to the excited populations $n^*_M$ (M=A,B) of the fluorophores in the observation slot which produce fluorescence at the rate $\eta_A n^*_A$ and $\eta_B n^*_B$, according to the quantum yields $\eta_M$ (M=A,B). The resultant fluorescence signal, F(t), is of the form $$F(t) = \sum_{k,M} \eta_M \alpha_{kM} L_k n_M \qquad \text{I}$$

where $\alpha_{kM}$ is the excitation efficiency of the fluorophore M by the laser of wavelength $\lambda_k$ (k=1,2). The efficiency parameters $\alpha_{kM}$ are proportional to the absorption coefficient of M at $\lambda_k$ and the lifetime of the excited state of molecule M. Because of mobility shifts, both A and B bands may appear in the observation slot at the same time and be excited by both lasers to a different degree, as given by the matrix $\alpha_{kM}$.

The entire signal F(t), produced by both kinds of molecules as excited by both lasers, is received by the photodetector. It may appear that since the received wavelength is not optically resolved, the information regarding the concentrations $n_A(t)$ and $n_B(t)$ is irretrievably lost. However, we recall that the received signal contains the response to two lasers modulated at different frequencies. Explicitly, we have:

$$F_{f1}=(\alpha_{1A}\eta_A n_A + \alpha_{1B}\eta_B n_B)L_{f1}; \qquad \text{II}$$

$$F_{f2}=(\alpha_{2A}\eta_A n_A + \alpha_{2B}\eta_B n_B)L_{f2}; \qquad \text{III}$$

Separation of these components in the electric domain is both efficient and exceedingly accurate. It can be done with high-quality narrow-band filters, as in a radio receiver with preset "stations". A better solution is to use heterodyne detection, with the local oscillator signal taken from the same source that drives the lasers in the first place.

Schematically, the frequency detection scheme with multicolor illumination is illustrated in FIG. 1. After the signal processing, e.g., by Fourier transform, the signal represents the amplitudes $F_{f1}$ and $F_{f2}$—slowly varying functions of time, from which the concentrations $n_A \equiv n_A(t)$ and $n_B \equiv n_B(t)$ are determined by solving the system of equations II and III. Evidently, the scheme is generalized to an arbitrary number of colors in a straightforward manner.

In a preferred embodiment, the present invention can include a combination of time-intensity-modulation of fluorescence and a wavelength-selective scheme.

Figure 3:
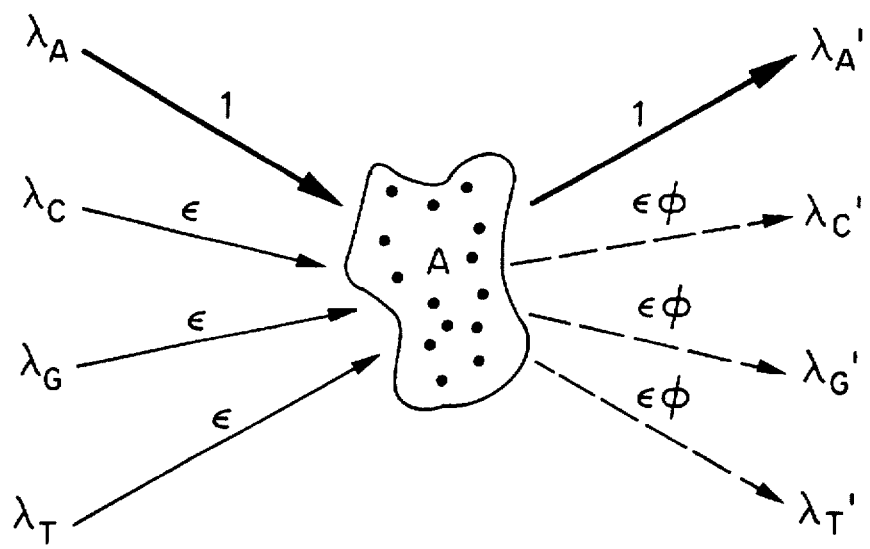
FIG. 3 is a schematic depicting the phenomenon of luminescence with multiple monochromatic light sources.

Cross-talk between different information channels in the conventional wavelength-selective scheme arises due to the fact that fluorophores of a particular kind (say, A labels) produce light not only at the wavelength $\lambda_A'$, referring to FIG. 3, corresponding to the fluorescence peak of A labels, but also at other wavelengths, selected by the optical filters at $\lambda_C'$, $\lambda_T'$, and $\lambda_G'$, as illustrated in FIG. 3. The parasitic signals are proportional to the overlap of the fluorescence spectra of the different dyes. See FIG. 2.

Fortunately, once the fluorescence has been converted to a robust electrical signal composed of the full spectra from all excitations, electrical operations can be performed which discriminate the contribution of each of the fluorophoretic emissions. A four component system will be used to demonstrate the present technique.

In the case of four lasers ($L_k$), the fluorophores are identified with label k=A, C, T, or G. In other words, $L_A$ is the output radiation of the laser "A", whose wavelength $\lambda_A$ is at the peak of the absorption spectrum of label A. The radiation $L_k$ is modulated at the radio frequency $f_k$, viz. $L_k(t) = L_{\lambda_k,f_k} \exp(2\pi i f_k t)$.

Irradiation of the observation slot by the four lasers gives rise to an excited population of the fluorophores, $$n^*_M(t) = \sum_k \alpha_{KM} L_K n_M,$$  IV where both indices k and M run over the same set of labels A, C, T, and G. The excited molecules produce fluorescence at the rate $\eta_{Mj} n_M^*$ where $\eta_{Mj}$ is the quantum yield coefficient of the fluorophore M into the wavelength channel $\lambda_j'$. The index j is also labeled by the fluorophore name, j=A, C, T, or G.

The total fluorescent signal received in the channel $\lambda_j'$ is given by $$F\lambda_j' = \sum_M \eta_{Mj} n^*_M = \sum_M \sum_k \eta_{Mj} \alpha_{kM} n_M L_k.$$  V If we were not able to discriminate between signals induced by different lasers, then our received signal structure would be described entirely by Eq. (V)—which is essentially similar to the conventional four-color detection scheme with wavelength selection. Determination of the quantities of interest, $n_M(t)$, is accomplished by operating on the signal to solve the system of four equations (V). The quality of data analysis is essentially dependent on the fact that the off-diagonal coefficients $\eta_{Mj}$ (j≠M) are smaller than the diagonal coefficients $\eta_{MM}$:

$$\frac{\eta_{Mj}}{\eta_{MM}} \equiv \phi_{Mj} < 1.$$  VI

Preferably, the conventional detection scheme will be enhanced when the wavelengths $\lambda_j'$ are spread apart so as to minimize the fluorescence overlap $\phi_{Mj}$. Simply, the scheme of modulated 4-color excitation, described above relies on the smallness of the absorption overlap, which implies that the off-diagonal coefficients $\alpha_{kM}$ (k≠M) are smaller than the diagonal coefficients $\alpha_{MM}$:

$$\frac{\alpha_{kM}}{\alpha_{MM}} \equiv \epsilon_{kM} < 1,$$  VII and the user benefits when the absorption peaks $\lambda_k$ are spread so as to minimize $\epsilon_{kM}$.

When the wavelength-selective detection of multicolor fluorescence is combined with frequency-selective detection of modulated multicolor excitation, then the information comes to us across 4×4=16 channels. Denoting by $F_{\lambda'_j,f_k}(t)$ the amplitude of the signal received by detector at wavelength $\lambda_j'$ after heterodyning with the local oscillator frequency $f_k$ the structure of the received data can be represented in the form:

$$S_{jk} = \sum_M \eta_{Mj} \alpha_{kM} n_M,$$  VIII where $S_{jk}(t)$ are slowly varying functions of time, $S_{jk} \equiv F_{\lambda'_j,f_k}/L_{\lambda_k f_k}$. The 16 equations (VIII) with 4 unknowns $n_M = n_M(t)$ form an overdetermined system. Needless to say, the overdetermination can be used to improve the signal to noise ratio. However, it is easy to see a dramatic improvement even if the full overdetermined stream of information is not used—but only its 4 diagonal channels, $S_{kk}$, are used. Using only diagonal elements means that identification is performed of frequency $f_k$ only in the optical channel, corresponding to wavelength $\lambda_j'$ with j=k. This leads to the four equations $$S_{MM} = \alpha_{MM} \eta_{MM} \left( n_M + \sum_{M' \neq M} \epsilon_{MM'} \phi_{M'M} n_{M'} \right)$$  IX Simple observation of the matrix in the right hand side of (IX)

| 1 | $\epsilon_{AC}\phi_{CA}$ | $\epsilon_{AG}\phi_{GA}$ | $\epsilon_{AT}\phi_{TA}$ | X |
| $\epsilon_{CA}\phi_{AC}$ | 1 | $\epsilon_{CG}\phi_{GC}$ | $\epsilon_{CT}\phi_{TC}$ | |
| $\epsilon_{GA}\phi_{AG}$ | $\epsilon_{GC}\phi_{CG}$ | 1 | $\epsilon_{GT}\phi_{TG}$ | | reveals that all small parameters that were of first order in the conventional scheme, have become of second order in smallness. The resultant signal improvement is as if the overlaps of the fluorescent spectra in the conventional scheme were reduced by additional small factors $\epsilon$; or as if in the multicolor modulated excitation scheme the overlap of absorption spectra were reduced by additional small factors $\phi$. Further improvement of signal acquisition is still available by using the "redundant" information which arrives in the 12 off-diagonal channels—in signals that are small to first order (by either the factor of $\phi$ or $\epsilon$).

An advantage of the alternative combined data acquisition scheme is illustrated schematically in FIG. 3 in the instance of the single group of fragments, labeled "A", passing through the observation slot. Simultaneous illumination by all four lasers results in a modulated fluorescence at all four frequencies. One of these signals (at wavelength $\lambda_A'$, modulated with the frequency $f_A$) is "strong", the rest are weaker by the corresponding $\epsilon$. Compared to the signal detected at the wavelength $\lambda_A'$ and heterodyned with the local oscillator frequency $f_A$, all other "diagonal" signals ($\lambda'_M, f_M$, M=C, G, or T) are weaker by the factors $\epsilon\phi$, which are second order in smallness.

Compared to either the conventional scheme, e.g., Smith, et al., which identifies labels by their fluorescent wavelength, or the invention frequency modulation scheme of FIG. 1, which identifies the same labels by their absorption wavelength, the combined method is somewhat more complex. However, the combined technique is capable of suppressing the channel cross-talk by at least one order of magnitude. Implementation of this technique provides for the realization of a fully automated data acquisition system.

Phase-resolved measurements employ a (radio) frequency modulated optical signal with a synchronous detection of the fluorescent response. The fluorescence lifetime, $\tau_F$, is determined from the phase shift between the detector and the source. Difference in the $\tau_F$ can be used for discriminating between dyes that do not possess an appreciable difference in their fluorescence spectra F. V. Bright and L. B. McGown, "Four Component Determinations Using Phase-Resolved Fluorescent Spectroscopy," *Anal. Chem.*, Vol. 57, pp. 55–59 (1984). Lakowicz and coworkers have demonstrated that 100% contrast discrimination can be accomplished with two dyes that differ only in their fluorescent lifetime, $\tau_F=4$ ns and $\tau_F=1.6$ ns (J. R. Lakowicz and K. W. Brendt, "Lifetime selective fluorescence imaging using an rf phase-sensitive camera" *Rev. Sci. Instrum.* 62, pp. 1727–1734, (1994); and J. R. Lakowicz, H. Szmacinski, K. Nowaczyk, K. W. Brendt and M. Johnson, "Flurescence lifetime imaging", *Nucleic Acids Res.* 18, pp. 4417–4421, (1992)). Phase-resolved detection suppresses the noise brought about by the parasitic fluorescence from (from glass, gel, fluids, etc.) provided the $\tau_F$ of the parasitic signal is different from that of the useful fluorescence.

Phase detection methods are ideally suited for use with semiconductor lasers modulated at multiple frequencies. In the above discussion of frequency-selective techniques, it has been assumed that each excitation wavelength $\lambda_k$ generated by laser $L_k$ has a one-to-one correspondence to the frequency $f_k$ at which this particular laser is modulated. Of course, it is precisely this correspondence which enables us to decode the origin of excitation. However, there is no reason, why there could not be more than one frequency associated with a given laser and the same wavelength. For example, communication lasers are typically modulated at a number of "carrier" frequencies with a total bandwidth of about 550 MHz, which permits the implementation of nearly 100 parallel channels (V. B. Gorfinkel and S. Luryi, "Fast data coding using modulation of interband optical properties by intersubband absorption in quantum wells," *Quantum Well Intersubband Transition Physics and Devices*, ed. by H. C. Liu, B. (1995)) with exceedingly demanding specifications on the cross-talk (for example, in a cable TV laser the combined intermodulation distortion from all channels into a given channel cannot exceed −60 dB relative to the carrier power in that channel).

A Multi-frequency grid method is straightforward and can be used as a model. Schematically the set of excitation signals is listed below:

| Laser | Wavelength | Modulation frequencies |
| --- | --- | --- |
| $L_A$ | $\lambda_A$ | $f_A^{(1)}, f_A^{(2)}, \ldots f_A^{(kA)}$ |
| $L_C$ | $\lambda_C$ | $f_C^{(1)}, f_C^{(2)}, \ldots f_C^{(kC)}$ |
| $L_G$ | $\lambda_G$ | $f_G^{(1)}, f_G^{(2)}, \ldots f_G^{(kG)}$ |
| $L_T$ | $\lambda_T$ | $f_T^{(1)}, f_T^{(2)}, \ldots f_T^{(kT)}$ |

The method is quite analogous to the well-developed technique of parameter extraction for device equivalent circuits, widely used in electronics (see, e.g., G. Kompa, "Modelling of dispersive microwave FET devices using quasi-static approach," *International Journ. of Microwave and Millimeter-Wave Computer Aided Eng.* 5, pp. 173–194 (1995)). With the parallel heterodyne detection of the set of responses at multiple frequencies we obtain not only the information about the relative amplitudes of the excitation at different wavelengths, but also the frequency dependence of the response to the same excitation wavelength. This information permits determination of the phase delay with a high accuracy. Moreover, this technique works well even with $2\pi f^*_M \tau_F \ll 1$. This feature is of particular interest in connection with sequencing environments where the effective $\tau_F$ is quenched to values as short as 0.1 ns—where the "conventional" phase detection would require special current drivers and a readout circuitry operating in the range of 1–2 GHz.

Figure 4:
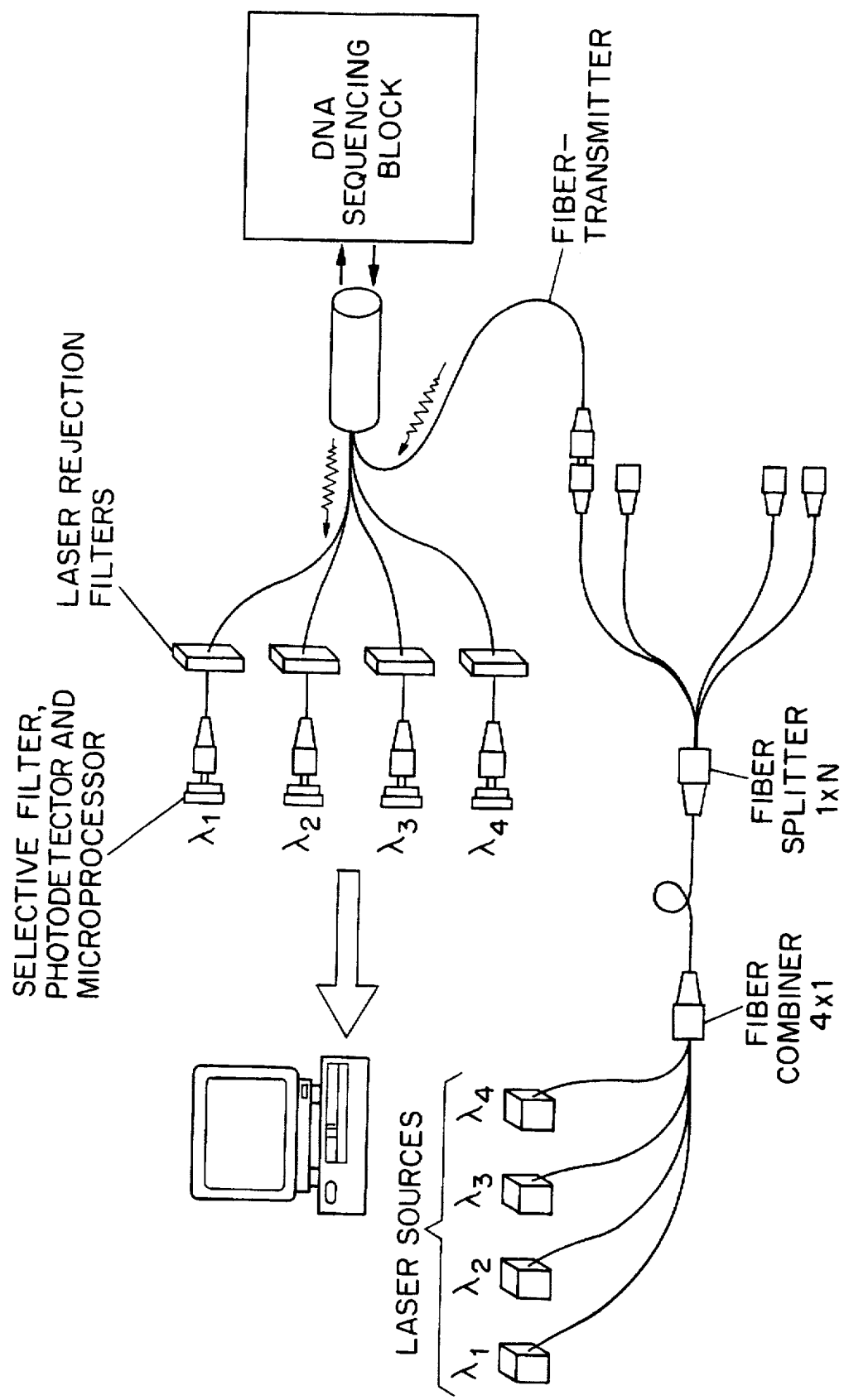
FIG. 4 is a schematic of a universal data acquisition system in accordance with the present invention.

A preferred data acquisition system with both multicolor excitation and multicolor detection is illustrated in FIG. 4. Four laser sources with intensity-modulated output are selected so as to provide the most efficient excitation of four fluorescent dyes. The laser radiation can be coupled into optical fibers, which are combined in a fiber bundle which delivers the radiation to the area of electrophoretic separation. Depending on the power requirements, a fiber splitter can be used to split the radiation into N channels, for parallel illumination of N sequencing lanes. Each fiber transmitter carrying the modulated radiation is packaged into an integrated fiber-optical probe—one probe per each lane (or capillary) of the sequencing machine. The fiber-transmitter structure permit focus of the radiation on a narrow spot (50–100 μm). The probe not only delivers the signal to the observation slot, but can also collect the fluorescent response from the slot. The response signal is then transmitted by fiber receiver to photodetectors, using the wavelength separation via optical fibers endowed with Fabry-Perot étalons (narrow-band pass filters) which are adapted to the fluorescent spectra of the four dyes. Narrow-band rejection filters can also be used to cut off spurious reflections of the laser radiation. The narrow-band pass filters and rejection filters are described hereinbelow in connection with FIGS. 6 and 7.

The photodetector demodulates the optical signal converting it to an electrical signal. The electrical signal is processed by a special-purpose microprocessor which provides the separation and amplification of different frequency components and the analog-to-digital conversion. The processed signal is delivered to a computer platform, where the automated base calling can be performed by specially developed software tools.

The proposed system structure permits the realization of all of the fluorescence detection methods discussed herein. The system will permit operation in the scanning mode, although this is not the preferred mode in view of the availability of inexpensive semiconductor lasers. The system can also be used with non-semiconductor lasers, which is essential for an early testing of different modules. Thus, the output of an argon-ion laser, radiating several wavelengths simultaneously, can be split between several channels and modulated at radio frequencies with external modulators.

The most developed class of semiconductor lasers used herein operates in the red and near infrared spectral range (wavelength $\lambda$ between 0.6 mm and 1.6 mm). Due to the high power density and reasonable spatial coherence of these lasers, it is possible to double their optical frequency into the blue part of the spectrum with the help of nonlinear crystals. However, the most significant potential for the use of semiconductor lasers lies in the fact that new fluorescent dyes can be excited in the red and near infrared. The wavelength range of these dyes ($\lambda$ between 0.65 mm and 0.8 mm) can be covered by commercially available semiconductor lasers.

Readily available red and infrared lasers work at room temperature. They are pumped by low-voltage current sources, generating up to 100 mW of power in the continuous wave (CW) regime. Semiconductor lasers have a small volume (typical dimensions 300x100x100 µm³). Together with a heat sink, the laser package is usually smaller than 1 cm³. From an ultra-narrow emitting area (about 10–20 µm²) they emit a very high radiation power density (up to megawatts MW/cm²). Because of the small area of emission, the semiconductor laser radiation can be easily focused on a small spot. Semiconductor lasers enable a wide variety of signal manipulations, which enhance the signal to noise ratio. Thus, one can modulate the amplitude of semiconductor laser radiation at frequencies of 10 GHz and even higher, generate, code, detect, and process arbitrary sequences of short pulses with the repetition rate of up to several Gbit/s, as well as generate ultra-short and powerful picosecond optical pulses.

It is clear that these features alone make semiconductor lasers attractive for use in DNA sequencing systems. Moreover, semiconductor lasers open new technical possibilities for the implementation of ultra-high performance data acquisition. These possibilities are based on the selective excitation of fluorescent dyes by an array of semiconductor lasers with different radiation wavelengths and output power modulated at different frequencies.

Selective excitation of fluorescence by a laser array can be accomplished by using an array of semiconductor lasers emitting at different wavelengths. Several different semiconductor lasers can be combined in a compact array. Taking infrared dyes with essentially different absorption peaks [such as BDS dyes CY5 ($\lambda$=650 nm) and CY7 (746 nm) or LI-COR dyes IRD-40 (769 nm) and IRD-41 (787 nm)] and choosing the appropriate radiation power ratio of the array laser, all four dye labels can essentially be balanced. By modulating the output radiation of the array lasers at different modulation frequencies, and using a synchronized signal processing technique, it is possible to significantly enhance the signal to noise ratio. Moreover, it appears feasible to detect and electronically separate the signals from different dyes, thus dramatically simplifying the optical part of the detection system.

Photomultiplier systems (J. A. Luckey, H. Drosman, A. J. Kostichka, D. A. Mead, J. D'cun, T. B. Norris and L. M. Smith. "DNA sequencing analysis of five genes ins A, B, C, D and E required for" *Nucleic Acids Res.*, 18, pp. 900–903, (1990)) and photodiode arrays (J. C. Gluckman, D. C. Shelly and M. V. Novotny. "Miniature fotometric photodiode array detection system for capillary chromatography," *Anal Chem*, 57, 1546–1552 (1985)), intensified photodiode arrays (D. F. Swaile and M. J. Sepaniak, *J. Microcolumn Separations*, 1, 155–158 (1989)), and charge coupled device camera systems (Y. F. Cheng, R. D. Picard and T. Vo-Dinh. "CCD CZE charged coupled device fluorescencedetection for capillary zone electrophoresis," *App. Spectrosc.* 11, pp. 755–765 (1990); J. V. Sweedler, J. B. Shear, H. A. Fishman, R. N. Zare and R. H. Scheller, "Fluorescence detection in capillary zone electrophoresis using a charge-coupled devices with time delayed integration," *Anal Chem*, 63, 496–502 (1991)). The most sensitive system using a two dimensional CCD camera for the detection of fluorescent labels was reported by Sweedler et al. Visible laser dyes are the main stay of present systems, but infrared dye based systems (S. A. Soper, Q. L. Mattingly and P. Vegnuta, "Photon burst detection of single near infrared fluorescent molecules," *Anal Chem*, 65, pp. 740–747 (1993); S. A. Soper, & Q. L. Mattingly, "Steady-state and picosecond laser fluorescence studies of nonradiative pathways in tricarbocianine dyes: implication to the design of near infrared fluorochromes with high fluorescence efficiencies," *I. Am. Chem. Soc.*, 116, pp. 3744–3752 (1993)) are also commercially available (LICOR) sophisticated signal processing algorithms are being developed for improving the base calling confidence; this remains a hot issue, and many different approaches are being explored by competing researchers.

The optical system, which continues to use distributed bulk optics, such as, microscope objectives, has not caught the imagination of many researchers, yet if any significant inroads are to be made toward increased throughput the optical system is a critical component in whole set up. The standard optical system uses a microscope objective to illuminate a small region in the flow cell, and a forward looking microscope objective based detection system defines probe volume of 10–100 pl. The LICOR system has taken a first step toward improving the optical system, their system combines the transmitting and receiving optics into a compact unit, which is placed on the same side of the slab gel. The unit is mounted onto a translational stage to allow scanning of several columns in a short period of time. However, as the number of columns increases, the increased scan time will cause two problems: firstly, the signal-to-noise ratio will decrease, requiring a longer integration time at each channel, which in turn will mean that data is not collected at the same instant of time from all columns. Finally the LICOR system cannot easily be adapted for use with a multi-capillary system. A fiber optic system using axial illumination of a capillary has been reported by Taylor and Yeung (1993), however, their system is invasive.

Figure 5:
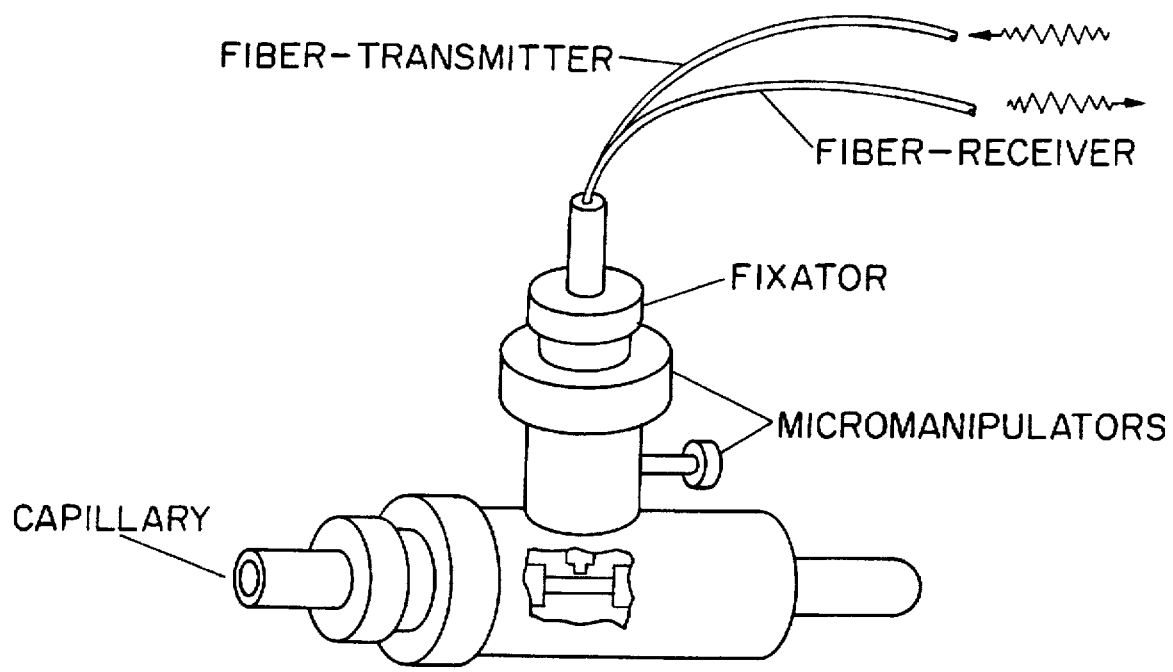
FIG. 5 depicts a T-shaped fiber-capillary connector of the present invention.

An improved optical system achieved by use of fiber optics, Dhadwahl, et al. H. S. Dhadwal, R. R. Khan, and M. A. Dellavecchia, "A Coherent Fiber Optic Sensor For Early Detection of Cataractogenesis in a Human Eye Lens," *Optical Engineering: special issue on Biomedical Engineering*, 32, pp. 223–238 (1993) [Also published in *Selected papers in Tissue Optics: Application in Medical Diagnostic and Therapy*, SPIE Milestone MS102 (1994)] and H. S. Dhadwal, K. Suh, and R. R. Khan. "Compact backscatter fiber optic systems for submicroscopic particle sizing," *Particulate Science and Technology: An International Journal*, 12, No. 2, pp. 139–148 (1994), is preferred to be used in connection with the present invention. Optical fibers offer a unique alignment and motion free capability for either multichannel capillary or slab gel based DNA sequencing systems. FIG. 5 shows a schematic of a T-shape connector which links the receiving and the transmitting fibers to an observation spot on a capillary. The capillary is held in position using a miniature 3-chuck jaw assembly; the fiber optical probe is positioned perpendicular to the capillary using the special fixtures shown. These allow 3 degrees of freedom for the alignment.

The assembly contains fibers both for the excitation of fluorescence (fiber transmitter) and the collection of the fluorescent response (fiber receiver). It is proposed here that the fiber receivers be endowed with a refractive index grating, so as to do discriminate between different wavelengths.

Figure 6:
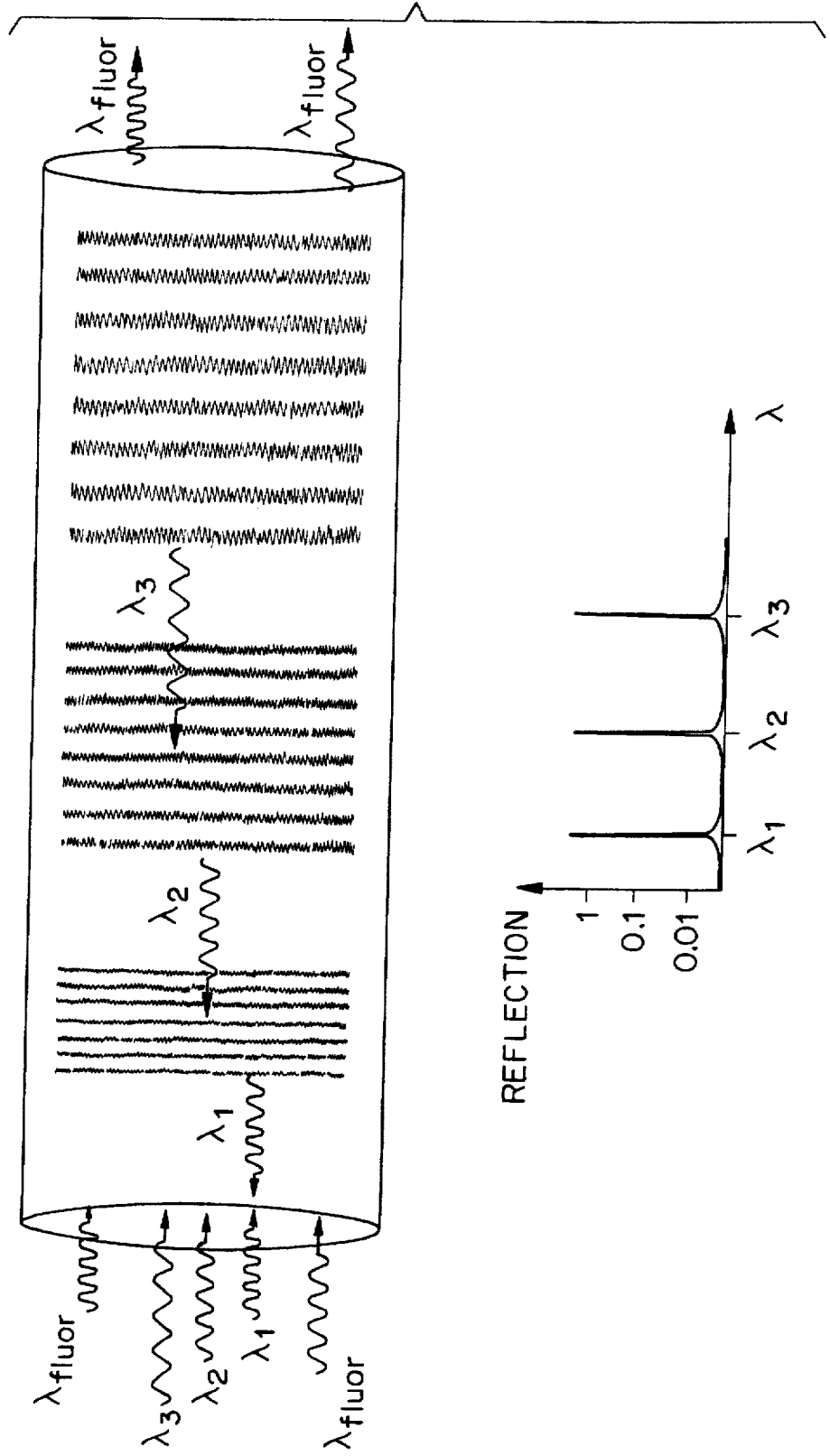
FIG. 6 depicts a fiber-receiver with a refractive index grading forming a set of one or more Bragg reflector for rejecting the stray (scattered or reflected) laser radiation.

Thus, FIG. 6 depicts a fiber with a refractive index profile along the fiber. This profile forms a set of one or more distributed Bragg reflectors designed so as to reject the light of wavelengths corresponding to the laser emission, $\lambda_1$, $\lambda_2$, and $\lambda_3$. The reflection spectrum of thus prepared fiber is depicted in the inset to FIG. 6.

FIG. 7 depicts a fiber endowed with a refractive index profile, corresponding to a Fabry-Perot resonator. Inset to FIG. 7 shows the transmission spectrum of such a fiber. The Fabry-Perot fiber is designed to select a desired wavelength of fluorescence, at $\lambda_0$ in the example depicted herein.

The choice of photodetector is determined by the fluorescent wavelength, for example, avalanche photodiode (APDS) have much higher quantum efficiencies at the near IR wavelength compared with photomultipliers. APDS are also more compact and easy to operate, but do need to be cooled to avoid non-linear gain effects due to self-heating. For visible wavelength, a photomultiplier may be the detector of choice. These are available in small packages which include built in high voltage biasing. In either case, the optical signal is easily and reliably coupled to the photodetector through the use of appropriate connectors.

The electronic read-out circuit which can be used in the present invention processes the output of the photodetectors to determine the digital equivalent of the fluorescence of the dyes, and can be used to transfer the digital signal to a desktop computer.

The analog to digital (A/D) conversion and the data formatting can be accomplished utilizing commercially available signal acquisition cards installed in the expansion slots of desk-top computers.

The read-out circuit can be designed such that it can be interfaces directly to common desktop computers through the system bus. A programmable input/output device can be used to format the data and interface to the computer. The card can be addressed by software similar to any other input/output device in the system. The prototype systems will be compatible with personal computers currently available.

Signal processing to estimate the sequence of nucleotide bases as accurately as possible can be attained by hardware circuits and/or software and software-assisted circuitry. These systems simultaneously process four digital data records corresponding to the A, C, G, and T bases, respectively. In addition to providing accurate calls, the methods also produce confidence levels which reflect the probabilities of correct calls.

Thus, while there have been described what are presently believed to be the preferred embodiments of the present invention, those skilled in the art will appreciate that modifications and changes made be made thereto without departing from the true spirit of the invention, and it is intended to include all such modifications and changes as come within the scope of the claims which are appended hereto.

What is claimed is:

1. A method of identifying a plurality of fluorophores having a different excitation spectra in a fluorophore containing substance comprising:
    a. stimulating at least one of the plurality of fluorophores with an incident optical signal fixed in relationship to a fluorophore substance holder, the incident optical signal having an optical spectrum comprising in spectral components wherein m is an integer greater than 1;
    b. modulating each of said spectral components in intensity according to a respective one of a set of linearly independent time-domain functions;
    c. exciting at least one of the plurality of fluorophores with at least one of said spectral components modulated in intensity according to said respective one of a set of linearly independent time-domain functions to produce fluorescence emission over a range of wavelengths;
    d. providing excitation efficiencies and fluorescence quantum yields for each of the plurality of fluorophores for each of the m spectral components;
    e. detecting substantially all of the entire fluorescence emission excited by the incident optical signal to produce a response signal which corresponds to the intensity of substantially all of said fluorescence emission over said range of wavelengths in the time-domain of the linearly independent time-domain functions; and
    f. analyzing the response signal utilizing the excitation efficiencies and quantum yields to identify at least one fluorophore of the plurality of fluorophores.

2. The method of claim 1 wherein said response signal is electrical.

3. The method of claim 2 wherein a photoreceiver converting said fluorescence emission to a corresponding electrical signal.

4. A method according to claim 1 wherein said spectral components of incident optical signal are substantially monochromatic.

5. A method according to claim 1 wherein the wavelengths of said spectral components of incident optical signal are known.

6. The method of claim 1 where the fluorescence emission is isolated from the radiation corresponding to said incident optical signal.

7. A method according to claim 1 wherein said m time-domain functions are analog functions.

8. A method according to claim 1 wherein said m time-domain functions are digital functions.

9. The method of claim 1 wherein said response signal is in the accoustical range.

10. A method according to claim 1 wherein at least one of the m spectral components of incident optical signal is modulated in intensity according to a respective time-domain function comprising a linear combination of n linearly independent time-domain basis functions, wherein n is an integer greater than 1.

11. A method according to claim 10 wherein each of the m spectral components of incident optical signal are modulated in intensity according to a respective time-domain function comprising a linear combination of $n_m$ linearly independent time-domain basis functions, where $n_m$ is an integer greater than 1.

12. The method of claim 11 wherein said response signal is analyzed to determined fluorescence lifetime.

13. A method according to claim 1 wherein each said excitation efficiency for each fluorophore is different from the excitation efficiency of another fluorophore.

14. A method according to claim 1 further comprising analyzing the response signal utilizing the excitation efficiencies and quantum yields to determine the amount of the at least one fluorophore of the plurality of fluorophores present in the fluorophore containing substance.

15. A method according to claim 1 wherein the response signal is analyzed according to $$F(t) = \sum_{K,M} \eta_M \alpha_{KM} L_K n_M$$

where F(t) is the fluorescence excited by the incident optical signal, $\eta_M$ is the quantum yield for a fluorophore M, $\alpha_{KM}$ is the excitation efficiency of a fluorophore M excited by a spectral component K having a wavelength $\lambda_K$, $n_M$ is the concentration of a fluorophore M and $L_K$ is the intensity of the spectral component K.

16. Apparatus for detecting a plurality of flurophores in a fluorophore containing substance comprising:
    a. a source of incident optical signal having an optical spectrum comprising m spectral components where m is an integer greater than 1, at least one of said spectral components capable of exciting fluorophores;
    b. modulator for modulating the intensity of each of said spectral components according to a respective one of a set of linearly independent time-domain functions;

c. a fluorophore substance holder for securing a fluorophore-containing substance fixed in relationship to said incident optical signal and making said fluorophore accessible to said incident optical signal from said source and for detection of fluorescence resulting from excitation of said fluorophores;

d. a detector optically coupled to said fluorophore substance holder for detection of substantially all of the fluorescence emitted by excited fluorophores and conversion of substantially all of said emitted fluorescence to an electrical signal; and e. means for analyzing the electrical signal utilizing provided quantities derived from excitation efficiencies and quantum yields for each of the fluorophores for each of the spectral components.

17. The apparatus of claim 16 which further comprises an optical filter element interposed between said fluorophore holder and said detector.

18. Apparatus according to claim 12 wherein said optical filter element comprises optical receiving fiber having a refractive index profile along the axis of the fiber with desired optical filter characteristics.

19. Apparatus according to claim 18 wherein said optical filter element comprises a Bragg reflector.

20. Apparatus according to claim 17 wherein said optical fiber element comprises a Fabry-Perot resonator.

21. The apparatus of claim 16 which comprises at least one transmitter optical fiber and at least one receiver optical fiber which are fixed in relation to said fluorophore substance holder for irradiating said fluorophore-containing substance and for detecting said fluorescence resulting from excitation of said fluorophore.

22. The apparatus of claim 21 where said fluorophore substance holder is a capillary and said optical transmitter and receiver fibers are fixed in relation to said capillary by means of T-shape connector.

23. The apparatus of claim 22 wherein said T-shape connector has degrees of freedom for three-dimensional alignment of said optical transmitter and receiver fibers in relation to said capillary.

24. Apparatus according to claim 16 wherein the means for analyzing the electrical signal analyzes the electrical signal according to $$F(t) = \sum_{K,M} \eta_M \alpha_{KM} L_K n_M$$

where F(t) is the fluorescence excited by the incident optical signal and converted by the detector into the electrical signal, $\eta_M$ is the quantum yield for a fluorophore M, $\alpha_{KM}$ is the excitation efficiency of a fluorophore M excited by a spectral component K having a wavelength $\lambda_K$, $n_M$ is the concentration of a fluorophore M and $L_K$ is the intensity of spectral component K.

* * * * *

UNITED STATES PATENT AND TRADEMARK OFFICE
CERTIFICATE OF CORRECTION

PATENT NO. :   5,784,157

DATED         :   July 21, 1998

INVENTOR(S) :   Gorfinkel et al.

It is certified that error appears in the above-identified patent and that said Letters Patent is hereby corrected as shown below:

First page of patent, under "U.S. Patent Documents," please add --5,171,534 12/92 Smith et al.--

Col. 13, line 51, "comprising in spectral" should read --comprising m spectral--.

Signed and Sealed this

Nineteenth Day of October, 1999

Attest:

Q. TODD DICKINSON

*Attesting Officer*    *Acting Commissioner of Patents and Trademarks*